US011639493B2

(12) United States Patent
Castro Cabrera

(10) Patent No.: US 11,639,493 B2
(45) Date of Patent: May 2, 2023

(54) CONSORTIUM OF BACTERIA THAT MINERALISES LIPIDS, STARCHES AND SUGARS (CARBOHYDRATES) AND ARE RESISTANT TO LETHAL DOSES OF THIODICARB (CARBAMATE) AND BIFENTHRIN (PYRETHROID) FOR INOCULATION INTO ORGANIC MATTER OF DIFFERENT ORIGINS

(71) Applicant: Salus Mundi Investments Limited, Mexico City (MX)

(72) Inventor: Luis Orlando Castro Cabrera, Mexico City (MX)

(73) Assignee: Salus Mundi Investments Limited, Mexico City (MX)

( * ) Notice: Subject to any disclaimer, the term of this patent is extended or adjusted under 35 U.S.C. 154(b) by 628 days.

(21) Appl. No.: 16/619,203

(22) PCT Filed: Jan. 30, 2019

(86) PCT No.: PCT/MX2019/000006
§ 371 (c)(1),
(2) Date: Dec. 4, 2019

(87) PCT Pub. No.: WO2019/160400
PCT Pub. Date: Aug. 22, 2019

(65) Prior Publication Data
US 2020/0172448 A1    Jun. 4, 2020

(30) Foreign Application Priority Data

Feb. 19, 2018  (MX) .................. MX/A/2018/002120

(51) Int. Cl.
| | |
|---|---|
| *C12N 1/20* | (2006.01) |
| *C05F 11/08* | (2006.01) |
| *C12N 1/36* | (2006.01) |
| *A01N 63/20* | (2020.01) |
| *A01N 63/22* | (2020.01) |
| *C12R 1/025* | (2006.01) |

(52) U.S. Cl.
CPC ............. *C12N 1/205* (2021.05); *A01N 63/20* (2020.01); *A01N 63/22* (2020.01); *C05F 11/08* (2013.01); *C12N 1/20* (2013.01); *C12N 1/36* (2013.01); *C12R 2001/025* (2021.05)

(58) Field of Classification Search
CPC ............. C12N 1/02; C12N 1/36; C12N 1/205; A01N 63/22; A01N 63/20; A01N 63/23; C12R 2001/025; C12R 2001/125; C12R 2001/06; C12R 2001/08; C12R 2001/075; C05F 11/08; B09C 1/10
See application file for complete search history.

(56) References Cited

U.S. PATENT DOCUMENTS

| 4,952,229 A * | 8/1990 | Muir ................................ 71/7 |
| 2011/0151508 A1* | 6/2011 | Lopez-Cervantes et al. .. 435/42 |
| 2011/0306116 A1 | 12/2011 | Jin et al. |
| 2012/0329650 A1 | 12/2012 | Lopez-Cervantes |
| 2013/0255338 A1 | 10/2013 | Lopez-Cervantes et al. |
| 2014/0212387 A1 | 7/2014 | Luth |
| 2016/0100587 A1 | 4/2016 | Bywater-Ekegard et al. |

FOREIGN PATENT DOCUMENTS

| MX | PA06003777 | 10/2008 |
| MX | 347762 | 11/2017 |
| WO | 2013148278 | 10/2013 |

OTHER PUBLICATIONS

Cycon M. et al., "Pyrethroid-Degrading Microorganisms and Their Potential for the Bioremediation of Contaminated Soils: A Review", Frontiers in Microbiology, Sep. 2016, vol. 7, article 1463, pp. 1-26. (Year: 2016).*
Orozco-Jaramillo, J. C. et al.,"Test of the seeding of nitrogen-fixing non-symbiotic microorganisms isolated from the rhizosphere of Pinus patula in Colombia," Alexander von Humboldt Biological Research Institute, La Florida Forest Station, Cota, Cundinamarca-Colombia, 2009, Bosque 30(2): 70-77.
Cuervo Lozado, J., "Isolation and Characterization of the *Bacillus* spp as biological nitrogen fixers and phosphate solubilizers in two samples of commercial biofertilizers," Dissertation, Pontificia Universidad Javeriana, Bogotá, Colombia, 2010.
Kabir, M. et al., "Identification of Azospirillum by oligonucleotide probes after isolation from soil and Sourghum rizoplan contaminated or not by the parasitic plant Siriga," 1995, NATO ASI Series, vol. G 37, pp. 479-485.
Kabir, M. et al., "Oligonucleotide probes based on 16S rRNA sequences for the identification of four *Azospirillum* species," 1995, Can. J. Microbiol., 41:1081-1087.
Validation of the Publication of New Names and New Combinations Previously Effectively Published Outside the IJSB, List No. 51, International Journal of Systematic Bacteriology, 1994.
Rivas, N. et al., "Bacterias promotoras del crecimiento vegetal en el cultivo del arroz (*Oryza sativa* L.). Perspectivas de su uso en Cuba," 2007, Cultivos Tropicales, vol. 28, No. 2, pp. 29-38.

(Continued)

*Primary Examiner* — Satyendra K Singh
(74) *Attorney, Agent, or Firm* — Preston Smirman; Smirman IP Law, PLLC

(57) ABSTRACT

The present invention provides a consortium of resistant microorganisms for biodegrading carbohydrates in the organic fraction of any source of solid waste. The genetic, metabolic and morphological structure of these resistant microorganisms works efficiently by biodegrading and mineralising solid biodegradable waste from municipal or harvest solid waste, reducing the production of gases and leachates. This compound enriches and increases the concentration of beneficial microorganisms, generating high-quality biological fertilisers suitable for use in agricultural production, in land recovery and conservation, under the parameters established in sustainable organic farming, which seeks to conserve, recover and use nature or the environment without generating the least negative impact.

2 Claims, No Drawings

(56) References Cited

OTHER PUBLICATIONS

Cycon, M. et al., "Pyrethroid-degrading microorganisms and their potential for the bioremediation of contaminated soils: a review," 2016, Frontiers in Microbiology, vol. 7, Article No. 1463.

Afshan, N-U-S et al., "Pesticide tolerant plant growth promoting rhizobacteria isolated from rhizosphere of okra," 2015, Soil Environ., vol. 34(2), pp. 111-118 (Abstract).

Ahmed, M. et al., "Analysis of bifenthrin degrading bacteria from rhizosphere of plants growing at tannery solid waste," 2015, American Journal of Plant Sciences, vol. 6, pp. 2042-2050.

Roy, T. et al., "Isolation, characterization and identification of two methomyl-degrading bacteria from a pesticide-treated crop field in West Bengal, India," 2017, Microbiology, vol. 86(6), pp. 753-764.

Mcclure, G. W. et al., "Degradation on phenylcarbamates in soil by mixed suspension of IPC-adapted microorganism," 1972, J. Environ. Quality, vol. 1(2), pp. 177-180.

Gong, T. et al., "An engineered Pseudomonas putida can simultaneously degrade organophosphates, pyrethroids and carbamates," 2018, Science of the Total Environment, vol. 628-629, pp. 1258-1265.

Asi, M. R. et al., "Compatability of entomorpathogenic fungi, Metarhizium anisopliae and Paecilomyces fumosoroseus with selective insecticides," 2010, Pakistan Journal of Botany, vol. 42(6), pp. 4207-4214.

Mohammadi, A. Y. et al., "The influence of pesticides and herbicides on the growth and spore gemrination of Trichoderma harzianum," 2015, Agriculture Science Development, vol. 4(3), pp. 41-44.

Abidin, A. F. et al., "Insecticide compatibility to the entomopathogenic fungi *Beauveria bassiana* and *Metarhizium anisopliae*," 2017, Scripta Biologica, vol. 4(4), pp. 273-279.

Thube, S. H. et al., "Compatability study of insecticides recommended for the management of tea mosquito bug *Helopeltis* spp. with bio-fungicide, *Trichoderma harzianum*," 2018, Journal of Entomology and Zoology Studies, vol. 6 (5), pp. 2034-2039.

International Search Report for PCT/MX2019/000005 dated Jun. 27, 2019.

International Search Report for PCT/MX2019/000007 dated Jun. 27, 2019.

International Search Report for PCT/MX2019/000006 dated Jun. 27, 2019.

Written Opinion of the International Searching Authority for PCT/MX2019/000005 dated Jun. 27, 2019.

Written Opinion of the International Searching Authority for PCT/MX2019/000007 dated Jun. 27, 2019.

Written Opinion of the International Searching Authority for PCT/MX2019/000006 dated Jun. 27, 2019.

International Preliminary Report on Patentability for PCT/MX2019/000005 dated Aug. 27, 2020.

International Preliminary Report on Patentability for PCT/MX2019/000007 dated Aug. 27, 2020.

International Preliminary Report on Patentability for PCT/MX2019/000006 dated Aug. 27, 2020.

Corrales, L. C. et al., "Efecto Biocontrolador de '*Bacillus*' spp., Frente a '*Fusarium*' sp., Bajo Condiciones de Invernadero en Plantas de Tomillo ('*Thymus Vulgaris* '.)," Nova, vol. 10(17), pp. 64-82.

\* cited by examiner

CONSORTIUM OF BACTERIA THAT MINERALISES LIPIDS, STARCHES AND SUGARS (CARBOHYDRATES) AND ARE RESISTANT TO LETHAL DOSES OF THIODICARB (CARBAMATE) AND BIFENTHRIN (PYRETHROID) FOR INOCULATION INTO ORGANIC MATTER OF DIFFERENT ORIGINS

CROSS-REFERENCE TO RELATED APPLICATION

The instant application is a national phase of PCT International Patent Application Serial No. PCT/MX2019/000006 filed Jan. 30, 2019, and claims priority to Mexican Patent Application Serial No. MX/a/2018/002120 filed Feb. 19, 2018, the entire specifications of both of which are expressly incorporated herein by reference.

INVENTION BACKGROUND

Since the TECHNIQUE STATUS regarding the scientific investigation and application of technology targeted to induce growth, repopulation and development of a consortium of beneficial microorganisms that can tolerate trace chemicals on soils and organic residues, and that are resistant to new generations of substances replacing conventional agrochemicals (forbidden in agriculture), is stated mainly in PATENT No. PA/2006/003777, issued by the IMPI (Apr. 27, 2017) where consortia of microorganisms resistant to organochlorinated and organophosphate compounds were isolated, in this new request developed an INVENTIVE ACTIVITY to develop, grow and select consortia of aerobic microorganisms resistant to chemical compounds in new generations of pesticides and biological control such as pyrethroid and carbamate compounds that are supposed to have a controlled use because of their secondary effects that pollute the soils, water mantles, and effect on agricultural development.

In this application, the INNOVATION is formed by developing a consortium of specific bacterial species, adapted to resist, and mineralize the organic matter polluted with carbamate such as thiodicarb and pyrethroids such as bifenthrin, these compounds are currently used in the agricultural and livestock industries, and are present more frequently in the organic matter contained in household solids (garbage). From the consortium biological processes, an organic substrate is produced that remediates soils from the deterioration produced and repopulates the soil with beneficial bacteria. It is worth mentioning that the microorganisms forming our consortia ARE NOT GENETICALLY MODIFIED nor are human, animal or plant pathogens.

With the use of organochlorinated and organophosphate compounds banned as pesticides on the second half of the twentieth century, carbamate and pyrethroid compounds become an alternative. Carbamate are pesticide substances formed by a N atom bonded to a labile group, the carbamic acid; its main characteristic is its high toxicity, low chemical stability and null build up on tissues; and pyrethroids are molecules with pesticide activity, they remain longer in the environment because the chemical modification of their formula makes them more stable under sunlight and to heat. These products are used indiscriminately in the agricultural and livestock industries, generating residues.

This research is outlined within the guidelines of the United Nation's Agenda 21 (Chapters 10, 11, 12 and 14, accordingly), regarding desertification and drought; agriculture and sustainable development. Calculations show that soil degradation on a world scale extends over 2000 million of hectares, endangering the way of life for over 1000 million people. Calculations show that approximately ⅔ of Earth's surface is dry land, with a limited fresh water supply, and a high percentage of these are eroded. Approximately 65% of the cultivable land has already lost a physical or a biological function.

In Latin America, indiscriminate use of agrochemicals for decades in agriculture has left residues, polluting the soil, surface and underground water. "Pesticides are designed to kill, reduce and repel insects, weeds, rodents, mushrooms and other organisms that could harm public health and the nation's economies. When these chemical products are handled or disposed improperly, they can harm human health". "The main risks linked to human health for being exposed chronically to small doses are related with cancer, birth defects, nervous and endocrine system disorders". Statements from: Childhood Pesticides Poisoning: Information for Advocacy and Action", UNEP Chemicals, May 2004.

Developing our scientific research, we have found soils with absence of micro loads caused by the excessive use of agrochemicals used on them. Example: Rice growing in the Ibaqué area (Colombia). Tomato growing in Sinaloa (México). Soy growing in the Santa Fe province (Argentina), among other cases.

The environmental awareness, ecological knowledge, attitudes and values towards the environment have been growing within our communities. The problem with municipal, home, agricultural and livestock solid residues keeps growing and its production is excessive, the lack of separation from the source, incorrect disposal, lack of areas to handle them and lack of treatment or recovery. Among the main problems caused by the production of gases that pollute the atmosphere, leachates that pollute the soils, underground water, surface water and generation of sources for disease or vehicles for disease transmission. The current solid organic residues from any source are very different to the ones produced 20 years ago related to the accumulation of trace chemicals, this toxicity is directly related to the pesticide, herbicide and acaricide evolution, among others.

International organizations, such as the FAO (Food and Agriculture Organization) and the WHO (World Health Organization), have established the maximum allowed levels of pesticide ingestion, however, national authorities in each country are responsible for establishing the proper legislation and carefully monitoring its use and the amount of residue through adequate analytical controls.

This is a scientific research with lipid, starch and sugar (carbohydrates) mineralizing bacteria from Dr. Luis Orlando Castro Cabrera's strain base, it is worth mentioning that the microorganisms used within this research were isolated originally by Dr. Luis Orlando Castro Cabrera's group according to patent 11851 from Colombia, such strains have been worked with since 1984.

The strains have been subjected to several stress stages using induced changes, adding traces to obtain chemical resistance to the synthetic pyrethroid bifenthrin (2-methyl biphenyl-3-ilmetil(2)-(1RS,3RS)-3-(2-chlorine 3,3,3-trifluoropropene)-2,2-dimethyl-cyclo-propane-carboxylate; alphanumeric code CA DPR Chem Code 2300. CAS 82657-04-3. CIPAC 415. FMC 54800. PC Code 128825) and the thiodicarb carbamate ($C_{10}H_{18}N_4O_4S_3$).

It is worth mentioning that the microorganism consortia here described have been deposited on Jun. 23, 2017 before the INIFAP at the National Center of Genetic Resources, having an address of Boulevard de la Biodiversidad No. 400, Col Rancho Las Cruces, CP 47600, Tepatitlan de Morelos, Jalisco, Mexico, under accession number by the INTERNATIONAL DEPOSIT AUTHORITY: CM-CNRG TB44 (a deposit certificate is annexed). The consortium as deposited under accession number CM-CNRG TB44 includes the following microorganisms: *Bacillus brevis, Bacillus subtilis, Bacillus thuringiensis* and *Arthrobacter globiformis*. More specifically, the consortium as deposited under accession number CM-CNRG TB44 consists of 10 to 25% of *Bacillus brevis,* 20 to 25% of *Bacillus subtilis,* 25 to 40% of *Bacillus thuringiensis* and 25 to 30% of *Arthrobacter globiformis*. Using these consortia for the production of fertilizers, we are supplying a safe and effective product for agricultural use to control pests as an alternative to chemical insecticides and pesticides.

The following isolation protocol for resistant strains and the formation of the microbial consortium shows that every one of the strains was evolved towards attained resistance WITHOUT GENOME MANIPULATION for each organism. On the other hand, each strain was isolated and selected independently through consecutive strain growth increasing the synthetic pyrethroid concentrations, such as bifenthrin and carbamates such as thiodicarb.

Percentages for each microorganism belonging to the consortium vary from 20 to 30% of the CFU for each of the strains. Amount variability will depend of the soil characteristics for the consortium.

PROCEDURE DESCRIPTION

To develop each of the research stages, logistics are defined with the two (2) groups of ingredients (thiodicarb and bifenthrin) as follows:

MATERIALS AND METHODS

Bacteria strains, nitrifiers, phosphorus solubilizers and antagonists for pathogens:

a) *Arthrobacter globiformis*
b) *Bacillus megaterium*
c) *Bacillus brevis*
d) *Bacillus thuringiensis*

Preparation for Stage Development

1. Glass material is sterilized in an autoclave.
2. The required amount of growth media is prepared, DFA Agar, Malt Agar (Corn Agar) and (PDA) to obtain viable colonies.
3. Lethal dose (LD) applied to a hectare is established, for thiodicarb as well as bifenthrin. 10 Petri dishes are prepared with 0.1 LD of thiodicarb of bifenthrin. Dishes are incubated at 25° C. for 72 hours with cold light.

Methodology a. Physical and chemical variables obtained in the research are maintained using traces. Petri dishes are placed inside the laminar flow chamber along with the diluted samples, to seed microorganisms in the dishes, a one ml sample of the strain is taken with an automated pipette, $10^{-1}$ and $10^{-2}$ solutions are performed and each solution is homogenized.
b. Having the petri dishes with the sterile and cold growth media, it is homogenized with 6 right to left movements, 6 clockwise movements, 6 counterclockwise movements and 6 front to back movements over a flat horizontal surface until the inoculum is completely integrated into the media, stand until it solidifies and each dish is covered with parafilm to avoid contamination during incubation.
c. The adapted consortium conditions are kept for the starting media (habitat), humidity, pH, temperature, chemical traceability, lighting and airing, Gram colorations and malachite green for the differentiation and observation of cellular structures.
d. Dishes with thiodicarb and Bifenthrin are placed inside the incubator at 25° C. for 72 hours with a cold light lamp.
e. Inoculated dishes are incubated for 72 hours and the bacteria growth will be recorded, the product concentration impact is determined over the plate growth (12 hours of incubation).
f. The residual impact of the product is reviewed after 7 days in the malt agar and PDA agar media.
g. If there is no growth over 10%, the process is repeated until a mortality under 90% is obtained.
h. The colony diameter is determined using a graduated ruler, data is recorded subtracting the diameter of the seeded dish, from which the effect over the mycelial growth will be determined compared to the control (not poisoned MA, denominated as percentage of inhibition of radial growth (PIRG %).
i. Progress is recorded daily and after 7 days analysis of an acceptable coverage is performed, if not, the procedure is repeated as many times as required.
j. From the 10 Petri dishes for each microorganism, the one with the lowest mortality is the one that will continue with the following study.
k. The study is performed again using this percentage until coverage increases and so on, the addition of thiodicarb and bifenthrin is alternated with the LD in intervals of 0.1 LD; all these experiments have been designed with the experimental strains and a control.
l. With the data obtained from the bacterial growth, the percentage of inhibition of gradual growth is obtained, the data is transformed for its analysis with the expression 2 arc sin. A two-way classification analysis of variance is applied and later the Turkey test is performed using a 5% probability.

RECORDS

Characteristics for this procedure were recorded during all stages through the following indicators:

a. Growth speed
b. Percentage of inhibition measured in Number of CFU/mm
c. Percentage of poison resistance

STAGES PERFORMED ON EACH MICROORGANISM

This research began with the 4 species of hydrocarbon and lipid mineralizing microorganisms that have already been introduced to an habitat change through continuous exposure for over 20 years to direct lighting (visible light) and to different conditions where a specific factor or nutrient was increased or decreased, producing a change and adaptation that allows it to work efficiently, having as limitations: time, temperature, pH, humidity and organic matter concentration, trace molecules and heavy metals present in agricultural soil and therefore, the organic fraction contained in household solid residue (garbage), livestock and agricultural residue.

For each species, stages analyzing times required to cover the entire field were performed. Once this time was determined, they were left to rest for 10 days to be later subject to the following protocol:

*Arthrobacter globiformis*

It's a Gram positive bacteria, non pathogenic, sporagenous, aerobic, its initial average size is 1.2 µm wide×2.5 µm long, optimal growth temperature varies from 20 to 30° C. Thrives in a pH from 6.5 to 7.0 and 90% humidity. The Arthrobacter sp. cells under complex media, undergo a notorious shape change through the growth cycle. Older growths are formed by coccoid cells, in other stages are bacillary. Cells are non-motile or motile through a polar flagellum or several lateral flagellums. Does not generate endospores. Chemoorganotroph. Form little or no acid from glucose. Bacteria commonly found in soil.

Habitat conditions are maintained, conditions obtained during the adaptation to organophosphorus and organochlorinated compounds and mercury of the microorganism, pH: 7.0, humidity: 35%, Temperature: Thermoresistant. These conditions are the starting point to adapt the strain to the new pollutants: thiodicarb (carbamate) and bifenthrin (pyrethroid).

Stages Performed in the Lab Using *Arthrobacter globiformis*

To adapt this microorganism, 40 stages were performed starting the processes with the conventional growth media. During stages E-1 and E-2 (Stage 1 and Stage 2) 0.1 LD (0.0000175 gr) of thiodicarb are added to the growth media. After incubation, a slow growth is recorded for 72 hours, until incubation day 45 with a mortality of 86%. The remaining 14% is under daily observation for 10 days to continue with the adaptation of this microorganism. Habitat humidity and temperature are maintained. (On stage 2, the same concentration of thiodicarb is used to strengthen the growth of resistant strains). The resistant strains are transferred to solid growth media with 0.2 LD (0.000035 gr) of thiodicarb (E-3 and E-4, again on E-4 the same concentration of thiodicarb is used to strengthen the growth of resistant strains) with a mortality between 66 to 80%. At the end of stage E-4, organisms have been selected for 152 days.

Stages E-5 and E-6 are subjected to the first addition of bifenthrin; 0.1 LD (0.00000006 gr) of bifenthrin are added, with a mortality of 84% (in the same way as the previous case, E-6 is used to strengthen the growth of resistant strains). On stages E-7 and E-8 bifenthrin is increased to 0.2 LD (0.00000012 gr) with a 75% mortality. At the end of E-8 (growth strengthening stage for the resistant strains) the adaptation process reaches 359 days.

On stages E-9 and E-10, 0.3 LD (0.000053 gr) of thiodicarb are added, with a mortality of 74%. (The same way as in previous stages, E-10 is used to strengthen the growth of resistant strains). On stages E-11 and E-12 0.4 LD (0.000070 gr) of thiodicarb are added, with a mortality rate of 71%. At the end of stage E-12 (growth strengthening stage for the resistant strains) the selection process reaches 530 days.

On stages E-13 and E-14, 0.3 LD (0.00000018 gr) of bifenthrin are added, with a mortality of 70% (The same way as in previous stages, E-14 is used to strengthen the growth of resistant strains). On stages E-15 and E-16, thiodicarb is increased to 0.4 LD (0.00000024 gr) with a 62% mortality. At the end of stage 16 (growth strengthening stage for the resistant strains) the selection process reaches 690 days.

On stages E-17 and E-18, 0.5 LD (0.000087 gr) of thiodicarb are added, with a mortality f 63% (The same way as in previous stages, E-18 is used to strengthen the growth of resistant strains). On stages E-19 and E-20, 0.6 LD (0.00011 gr) of thiodicarb are added, with a mortality rate of 58%. At the end of stage E-20 (growth strengthening stage for the resistant strains) the selection process reaches 843 days.

On stages E-21 and E-22, 0.5 LD (0.00000030 gr) of bifenthrin are added, with a mortality of 56% (The same way as in previous stages, E-22 is used to strengthen the growth of resistant strains). On stages E-23 and E-24, thiodicarb is increased to 0.6 LD (0.00000036 gr) with a mortality rate of 48%. At the end of stage 24 (growth strengthening stage for the resistant strains) the selection process reaches 982 days.

On stages E-25 and E-26, 0.7 LD (0.00012 gr) of thiodicarb are added, with a mortality of 48% (The same way as in previous stages, E-26 is used to strengthen the growth of resistant strains). On stages E-27 and E-28, 0.8 LD (0.00014 gr) of thiodicarb are added, with a mortality rate of 40%. At the end of stage E-28 (growth strengthening stage for the resistant strains) the selection process reaches 1110 days.

On stages E-29 and E-30, 0.7 LD (0.00000036 gr) of bifenthrin are added, with a mortality from 40% (The same way as in previous stages, E-30 is used to strengthen the growth of resistant strains). On stages E-31 and E-32, thiodicarb is increased to 0.8 LD (0.00000042 gr) with a mortality rate from 36%. At the end of stage 30 (growth strengthening stage for the resistant strains) the selection process reaches 1239 days.

On stages E-33 and E-34, 0.9 LD (0.00016 gr) of thiodicarb are added, with a mortality of 32% (The same way as in previous stages, E-34 is used to strengthen the growth of resistant strains). On stages E-35 and E-36, 1 LD (0.00018 gr) of thiodicarb are added, with a mortality rate of 25%. At the end of stage E-36 (growth strengthening stage for the resistant strains) the selection process reaches 1362 days.

On stages E-37 and E-38, 0.9 LD (0.00000042 gr) of bifenthrin are added, with a mortality of 25% (The same way as in previous stages, E-38 is used to strengthen the growth of resistant strains). On stages E-39 and E-40, thiodicarb is increased to 1 LD (0.00000048 gr) with a mortality rate of 18%. At the end of stage 40 (growth strengthening stage for the resistant strains) the selection process reaches 1479 days.

During the development of this research, performed in a term over 4 years long, the strains were subjected to a physical media change, adapting them to withstand increasing concentrations of thiodicarb and bifenthrin. These tests result in an initial mortality close to 82%.

Having the microorganism already adapted to the media with the previously mentioned characteristics, the purity of the strain is verified, taking 0.1 ml from the bacterial suspension, a dish with TSA (Tryptic Soy Agar) is seeded and incubated at 52° C.+/−2° C., its motility is verified with colouring with Gram and malachite green. Once the purity of the strain to be worked with is determined, the process of making a suspension with this microorganism begins, in a TSA dish, incubated at 52° C.+/−2° C. for 36 to 48 hours, later, with a sterile swab, a sample is taken and seeded in an Erlenmeyer flask with 100 ml of the media previously adding 0.01% of thiodicarb and bifenthrin traces, stirred at 170 rpm and 37° C. for 4 hours; then the biomass is resuspended in 50 ml of the different lyoprotectant solutions homogenizing the media, the CFU/ml count is performed. This inoculum, previously protected, is taken to the incubator and reseeded periodically in a new growth media, procedure performed in time intervals going from 72 hours to 120 hours. The time maintaining the same conditions is used to perform general observations. These strains are maintained in an active growth media, adding a previously sterilized mineral oil, to guarantee the required humidity.

*Bacillus subtillis*

It is a Gram positive bacillus, sporogenous, strictly aerobic, with a thick murein layer, its initial average size is 0.75 µm wide×0.9 µm long; its growth environmental temperatures go from 15 to 55° C., *B. subtilis*' natural habitat is the soil, with great temperature fluctuations. However, the cells from this microorganism are subjected to a phenotypic change when temperature is modified from 30° C. to 45° C. or 80° C. Its activity is developed within a pH from 4.7 to 5.5, humidity from 70 to 80% and tolerates minimal trace toxic concentrations.

It is used to produce an antibiotic called bacitracin, acts against Gram negative damaging its cellular membrane and inhibiting the wall formation. Besides the enzyme production such as bacterial amylase, useful in the paper and textile industries, and enzyme used to tan leathers, remove stains and soften meats.

A microcosmos Model (Kabir and Cols, 1995) was used to isolate these microorganisms. The strains were classified using traditional methods (Numeric taxonomy) and immunochemicals (indirect immunofluorescence-IIF, according to Llewot and Stead, 1991). Pure strains were used from different areas. The growth media used for the *B. subtillis* is a nutritious media, with 5% of soy-agar maintaining parameters such as pH, minimum oxygen levels, humidity and temperature from its original conditions.

Stages Performed in the Lab for *B. subtillis*

Beginning with habitat conditions obtained in the adaptation to organophosphate, organochlorine compounds and mercury from the microorganisms at the E-38 pH: 7.2, Humidity: 36%, thermoresistant and aerobic. These conditions are the starting point to adapt the strain to thiodicarb and bifenthrin.

To adapt this microorganism, 40 stages were performed, beginning the process with the conventional growth media. During stages E-1 and E-2 (Stage 1 and Stage 2) 0.1 LD (0.0000175 gr) of thiodicarb. After incubation a slow growth is seen for the first 72 hours. Until day 68 of incubation mortality is at 82% and on stage E-2 at 80%. The remaining 20% is maintained for 10 days under daily observation to continue with the microorganism adaptation. Habitat temperature and humidity are maintained. (On stage 2, the same concentration of thiodicarb is used to strengthen the growth of resistant strains). The resistant strains are transferred to solid growth media with 0.2 LD (0.000035 gr) of thiodicarb (E-3 and E-4, again on E-4 the same concentration of thiodicarb is used to strengthen the growth of resistant strains) with a mortality rate from 75 to 72%. At the end of stage E-4, organisms have been selected for 294 days. Stages E-5 and E-6 are subjected to the first addition of bifenthrin; 0.1 LD (0.00000006 gr) of bifenthrin are added, with a mortality rate from 72 to 71% (in the same way as the previous case, E-6 is used to strengthen the growth of resistant strains). On stages E-7 and E-8 bifenthrin is increased to 0.2 LD (0.00000012 gr) with a mortality from 70 to 68%. At the end of E-8 (growth strengthening stage for the resistant strains) the adaptation process reaches 570 days.

On stages E-9 and E-10, 0.3 LD (0.000053 gr) of thiodicarb are added, with a mortality from 66 to 63%. (The same way as in previous stages, E-10 is used to strengthen the growth of resistant strains). On stages E-11 and E-12 0.4 LD (0.000070 gr) of thiodicarb are added, with a mortality rate from 64 to 62%. At the end of stage E-12 (growth strengthening stage for the resistant strains) the selection process reaches 827 days.

On stages E-13 and E-14, 0.3 LD (0.00000018 gr) of bifenthrin are added, with a mortality of 65% (The same way as in previous stages, E-14 is used to strengthen the growth of resistant strains). On stages E-15 and E-16, thiodicarb is increased to 0.4 LD (0.00000024 gr) with a mortality from 64 to 60%. At the end of stage 16 (growth strengthening stage for the resistant strains) the selection process reaches 1071 days.

On stages E-17 and E-18, 0.5 LD (0.000087 gr) of thiodicarb are added, with a mortality from 59 to 54% (The same way as in previous stages, E-18 is used to strengthen the growth of resistant strains). On stages E-19 and E-20, 0.6 LD (0.00011 gr) of thiodicarb are added, with a mortality rate from 52 to 50%. At the end of stage E-20 (growth strengthening stage for the resistant strains) the selection process reaches 1283 days.

On stages E-21 and E-22, 0.5 LD (0.00000030 gr) of bifenthrin are added, with a mortality from 47 to 45% (The same way as in previous stages, E-22 is used to strengthen the growth of resistant strains). On stages E-23 and E-24, thiodicarb is increased to 0.6 LD (0.00000036 gr) with a mortality rate from 40 to 35%. At the end of stage 24 (growth strengthening stage for the resistant strains) the selection process reaches 1458 days.

On stages E-25 and E-26, 0.7 LD (0.00012 gr) of thiodicarb are added, with a mortality from 35 to 30% (The same way as in previous stages, E-26 is used to strengthen the growth of resistant strains). On stages E-27 and E-28, 0.8 LD (0.00014 gr) of thiodicarb are added, with a mortality rate from 28 to 25%. At the end of stage E-28 (growth strengthening stage for the resistant strains) the selection process reaches 1581 days.

On stages E-29 and E-30, 0.7 LD (0.00000036 gr) of bifenthrin are added, with a mortality from 25 to 23% (The same way as in previous stages, E-30 is used to strengthen the growth of resistant strains). On stages E-31 and E-32, thiodicarb is increased to 0.8 LD (0.00000042 gr) with a mortality rate from 20 to 18%. At the end of E-32 (growth strengthening stage for the resistant strains) the selection process reaches 1704 days.

On stages E-33 and E-34, 0.9 LD (0.00016 gr) of thiodicarb are added, with a mortality from 18 to 15% (The same way as in previous stages, E-34 is used to strengthen the growth of resistant strains). On stages E-35 and E-36, 1 LD (0.00018 gr) of thiodicarb are added, with a mortality rate from 12 to 9%. At the end of stage E-36 (growth strengthening stage for the resistant strains) the selection process reaches 1327 days.

On stages E-37 and E-38, 0.9 LD (0.00000042 gr) of bifenthrin are added, with a mortality from 8 to 6% (The same way as in previous stages, E-38 is used to strengthen the growth of resistant strains). On stages E-39 and E-40, thiodicarb is increased to 1 LD (0.00000048 gr) decreasing mortality to 5%. At the end of stage 40 the selection process reaches 1882 days; 5.6 years of research.

TABLE NO. 1

Comparative Table, Initial and Final Characteristics
DEVELOPMENT CHARACTERISTICS *Bacillus subtillis*

| PARAMETER | INITIAL | FINAL |
|---|---|---|
| pH | 4.5-5.5 | 7.2 |
| Humidity | 80% | 36% |
| Respiration | Aerobic | Aerobic |
| Temperature | Thermoresistant | Thermoresistant |
| Resistant to: | Organochlorinated, organic phosphorus compounds and mercury | 1 LD of thiodicarb and bifenthrin |
| Size | 0.9 × 1.3 μm | 0.9 × 1.2 μm |
| Bio degradation time | 120 days | 35 days |

At the end of the adaptation process, the microorganism shows normal activity in said media with traces of phosphorus ($P_2O_5$) in its cellular membrane.

Also shows that the organic material formed by 80% of carbohydrates stabilizes in an average of 35 days unlike the wild microorganism that takes 120 days.

Bacillus brevis

It is a non-pathogenic Gram positive bacilli, sporogenous, facultative anaerobic, its initial average size is 0.85 μm wide×1.2 μm long, its optimal environmental growth temperature varies from 21 to 37° C., and with a total absence of oxygen. It is active within a pH from 2.0 to 4.5, average humidity of 80%. This microorganism is taken from the rumen. The B. brevis cells produce gramicidin, an antibiotic used against Gram positive bacteria. The growth media used for B. brevis is conventional, direct oxygenation and radiation is maintained, humidity and temperature obtained in previous development.

Stages Performed in the Lab for Bacillus brevis

Beginning with habitat conditions obtained in the adaptation to organophosphate, organochlorine compounds and mercury from the microorganisms at the E-38 pH: 7.2, Humidity: 36%, thermoresistant and facultative anaerobic. These conditions are the starting point to adapt the strain to thiodicarb and bifenthrin.

To adapt this microorganism, 51 stages were performed, beginning the process with the conventional growth media. During stages E-1 and E-2 (Stage 1 and Stage 2) 0.1 LD (0.0000175 gr) of thiodicarb. After incubation a slow growth is seen for the first 72 hours. Until day 68 of incubation mortality is 82% and on stage E-2 at 78%. The remaining 20% is maintained for 10 days under daily observation to continue with the microorganism adaptation. Habitat temperature and humidity are maintained. (On stage 2, the same concentration of thiodicarb is used to strengthen the growth of resistant strains). The resistant strains are transferred to solid growth media with 0.2 LD (0.000035 gr) of thiodicarb (E-3 and E-4, again on E-4 the same concentration of thiodicarb is used to strengthen the growth of resistant strains) with a mortality rate of 72%. At the end of stage E-4, organisms have been selected for 186 days.

Stages E-5 and E-6 are subjected to the first addition of bifenthrin; 0.1 LD (0.00000006 gr) of bifenthrin are added, with a mortality rate of 73% (in the same way as the previous case, E-6 is used to strengthen the growth of resistant strains). On stages E-7 and E-8 bifenthrin is increased to 0.2 LD (0.00000012 gr) with a mortality from 70 to 68%. At the end of E-8 (growth strengthening stage for the resistant strains) the adaptation process reaches 430 days.

On stages E-9 and E-10, 0.3 LD (0.000053 gr) of thiodicarb are added, with a mortality of 68%. (The same way as in previous stages, E-10 is used to strengthen the growth of resistant strains). On stages E-11 and E-12 0.4 LD (0.000070 gr) of thiodicarb are added, with a mortality rate from 67%. At the end of stage E-12 (growth strengthening stage for the resistant strains) the selection process reaches 648 days.

On stages E-13 and E-14, 0.3 LD (0.00000018 gr) of bifenthrin are added, with a mortality of 67% (The same way as in previous stages, E-14 is used to strengthen the growth of resistant strains). On stages E-15 and E-16, thiodicarb is increased to 0.4 LD (0.00000024 gr) with a mortality of 60%. At the end of stage 16 (growth strengthening stage for the resistant strains) the selection process reaches 853 days.

On stages E-17 and E-18, 0.5 LD (0.000087 gr) of thiodicarb are added, with a mortality from 59 to 54% (The same way as in previous stages, E-18 is used to strengthen the growth of resistant strains). On stages E-19 and E-20, 0.6 LD (0.00011 gr) of thiodicarb are added, with a mortality rate of 55%. At the end of stage E-20 (growth strengthening stage for the resistant strains) the selection process reaches 1057 days.

On stages E-21 and E-22, 0.5 LD (0.00000030 gr) of bifenthrin are added, with a mortality of 55% (The same way as in previous stages, E-22 is used to strengthen the growth of resistant strains). On stages E-23 and E-24, thiodicarb is increased to 0.6 LD (0.00000036 gr) with a mortality rate of 51%. At the end of stage 24 (growth strengthening stage for the resistant strains) the selection process reaches 1245 days.

On stages E-25 and E-26, 0.7 LD (0.00012 gr) of thiodicarb are added, with a mortality of 50% (The same way as in previous stages, E-26 is used to strengthen the growth of resistant strains). On stages E-27 and E-28, 0.8 LD (0.00014 gr) of thiodicarb are added, with a mortality rate of 46%. At the end of stage E-28 (growth strengthening stage for the resistant strains) the selection process reaches 1409 days of adaptation.

On stages E-29 and E-30, 0.7 LD (0.00000036 gr) of bifenthrin are added, with a mortality of 44% (The same way as in previous stages, E-30 is used to strengthen the growth of resistant strains). On stages E-31 and E-32, thiodicarb is increased to 0.8 LD (0.00000042 gr) with a mortality rate of 42%. At the end of E-32 (growth strengthening stage for the resistant strains) the selection process reaches 1568 days.

On stages E-33 and E-34, 0.9 LD (0.00016 gr) of thiodicarb are added, with a mortality of 38% (The same way as in previous stages, E-34 is used to strengthen the growth of resistant strains). On stages E-35 and E-36, 1 LD (0.00018 gr) of thiodicarb are added, with a mortality rate of 28%. At the end of stage E-36 (growth strengthening stage for the resistant strains) the selection process reaches 1702 days of adaptation.

On stages E-37 and E-38, 0.9 LD (0.00000042 gr) of bifenthrin are added, with a mortality of 26% (The same way as in previous stages, E-38 is used to strengthen the growth of resistant strains). On stages E-39 and E-40, thiodicarb is increased to 1 LD (0.00000048 gr) decreasing mortality of 20%. At the end of stage 40 the selection process reaches 1828 days. 5 years of research.

On stages E-41 and E-42, 1.1 LD (0.00020 gr) of thiodicarb are added, with a mortality of 28% (The same way as in previous stages, E-42 is used to strengthen the growth of resistant strains). On stages E-43 and E-44, 1.2 LD (0.00022 gr) of thiodicarb are added, with a mortality rate on both stages of 22%. At the end of stage E-44 (growth strengthening stage for the resistant strains) the selection process reaches 1962 days of adaptation.

On stages E-45 and E-46, 1.1 LD (0.00000054 gr) of bifenthrin are added, with a mortality of 20% (The same way as in previous stages, E-46 is used to strengthen the growth of resistant strains). On stages E-47 and E-48, thiodicarb is increased to 1.2 LD (0.00000060 gr) decreasing mortality of 12%. At the end of stage 48 (growth strengthening stage for the resistant strains) the selection process reaches 2056 days of adaptation.

On stages E-49 and E-50, 1.3 LD (0.00024 gr) of thiodicarb are added, with a mortality of 10% (The same way as in previous stages, E-50 is used to strengthen the growth of resistant strains). On stages E-51, 1.3 LD (0.00024 gr) of thiodicarb are added. At the end of stage E-51 the selection process reaches 2112 days of adaptation.

TABLE NO. 2

Comparative Table, Initial and Final Characteristics
DEVELOPMENT CHARACTERISTICS *Bacillus brevis*

| PARAMETER | INITIAL | FINAL |
|---|---|---|
| pH | 7.2 | 7.2 |
| Humidity | 80% | 36% |
| Respiration | Facultative anaerobic | Facultative anaerobic |
| Temperature | 15-55° C. | 52-75° C. |
| Resistant to: | Organochlorinated, organophosphorus compounds and mercury | 1.3 LD of thiodicarb and bifenthrin |
| Size | 0.9 × 1.2 µm | Size 0.9 × 1.2 µm |
| Biodegradation time | 35 days | 35 Days |

At the end of the adaptation process, the microorganism shows normal activity in such media, finding traces of phosphorus ($P_2P_5$) in its cellular membrane. Organic matter formed in 80% by carbohydrates stabilizes in an average of 35 days unlike the wild microorganism (control) for which the time was 120 days.

*Bacillus thuringiensis*

It is a non-pathogenic Gram positive bacilli, sporogenous, facultative anaerobic, its initial average size is 1.2 µm wide×4.8 µm long, its optimal environmental growth temperature varies from 10 to 45° C., its cellular membrane is completely smooth and its activity is developed within a pH of 6.5 to 7.2 with 60% humidity.

The *B. thuringiensis* cells form crystalline appositions visible with an optical microscope. These crystalline appositions are formed by protoxins that contain d-endotoxins, with pesticide activity specific against insects. Some varieties of *Bacillus thuringiensis* can also produce another toxin, the b-exotoxin. It is a toxin produced during vegetative growth which is a nucleotide byproduct from the adenine that works as an RNA polymerase inhibitor. But the use of this toxin is not allowed in some countries because it is also toxic to mammals.

The growth media for the *B. thuringiensis* is a nutritious media, with 5% of soy-agar maintaining parameters such as pH, minimum oxygen levels, humidity and temperature from its original conditions.

Stages Performed in the Lab for *B. thuringiensis*

Beginning with habitat conditions obtained in the adaptation to organophosphate, organochlorine compounds and mercury from the microorganisms at the E-38 pH: 7.2, Humidity: 52%, thermoresistant (74° C.), pH 7.0 and facultative anaerobic. These conditions are the starting point to adapt the strain to thiodicarb and bifenthrin. During all stages a cold light lamp will be used to adapt the microorganism to sunlight.

To adapt this microorganism, 48 stages were performed, beginning the process with the conventional growth media. During stages E-1 and E-2 (Stage 1 and Stage 2) 0.1 LD (0.0000175 gr) of thiodicarb. After incubation a slow growth is seen for the first 72 hours. Until day 45 of incubation mortality is from 72 to 70%. The remaining 30% is maintained for 10 days under daily observation to continue with the microorganism adaptation. Habitat temperature and humidity are maintained. (On stage 2, the same concentration of thiodicarb is used to strengthen the growth of resistant strains). The resistant strains are transferred to solid growth media with 0.2 LD (0.000035 gr) of thiodicarb (E-3 and E-4, again on E-4 the same concentration of thiodicarb is used to strengthen the growth of resistant strains) with a mortality rate from 70 to 68%. At the end of stage E-4, organisms have been selected for 282 days.

Stages E-5 and E-6 are subject to the first addition of bifenthrin; 0.1 LD (0.00000006 gr) of bifenthrin are added, with a mortality rate from 68 to 65% (in the same way as the previous case, E-6 is used to strengthen the growth of resistant strains). On stages E-7 and E-8 bifenthrin is increased to 0.2 LD (0.00000012 gr) with a mortality from 64 to 63%. At the end of E-8 (growth strengthening stage for the resistant strains) the adaptation process reaches 565 days.

On stages E-9 and E-10, 0.3 LD (0.000053 gr) of thiodicarb are added, with a mortality from 65 to 61%. (The same way as in previous stages, E-10 is used to strengthen the growth of resistant strains). On stages E-11 and E-12 0.4 LD (0.000070 gr) of thiodicarb are added, with a mortality rate from 57 to 55%. At the end of stage E-12 (growth strengthening stage for the resistant strains) the selection process reaches 822 days.

On stages E-13 and E-14, 0.3 LD (0.00000018 gr) of bifenthrin are added, with a mortality from 57 to 55% (The same way as in previous stages, E-14 is used to strengthen the growth of resistant strains). On stages E-15 and E-16, thiodicarb is increased to 0.4 LD (0.00000024 gr) with a mortality from 52 to 50%. At the end of stage 16 (growth strengthening stage for the resistant strains) the selection process reaches 1064 days.

On stages E-17 and E-18, 0.5 LD (0.000087 gr) of thiodicarb are added, with a mortality from 52 to 50% (The same way as in previous stages, E-18 is used to strengthen the growth of resistant strains). On stages E-19 and E-20, 0.6 LD (0.00011 gr) of thiodicarb are added, with a mortality rate from 50 to 45%. At the end of stage E-20 (growth strengthening stage for the resistant strains) the selection process reaches 1280 days.

On stages E-21 and E-22, 0.5 LD (0.00000030 gr) of bifenthrin are added, with a mortality from 50 to 45% (The same way as in previous stages, E-22 is used to strengthen the growth of resistant strains). On stages E-23 and E-24, thiodicarb is increased to 0.6 LD (0.00000036 gr) with a mortality rate from 44 to 42%. At the end of stage 24 (growth strengthening stage for the resistant strains) the selection process reaches 1467 days.

On stages E-25 and E-26, 0.7 LD (0.00012 gr) of thiodicarb are added, with a mortality from 44 to 40% (The same way as in previous stages, E-26 is used to strengthen the growth of resistant strains). On stages E-27 and E-28, 0.8 LD (0.00014 gr) of thiodicarb are added, with a mortality rate from 36 to 35%. At the end of stage E-28 (growth strengthening stage for the resistant strains) the selection process reaches 1633 days of adaptation.

On stages E-29 and E-30, 0.7 LD (0.00000036 gr) of bifenthrin are added, with a mortality from 36 to 33% (The same way as in previous stages, E-30 is used to strengthen the growth of resistant strains). On stages E-31 and E-32, thiodicarb is increased to 0.8 LD (0.00000042 gr) with a mortality rate from 30 to 28%. At the end of E-32 (growth strengthening stage for the resistant strains) the selection process reaches 1777 days.

On stages E-33 and E-34, 0.9 LD (0.00016 gr) of thiodicarb are added, with a mortality of 30% (The same way as in previous stages, E-34 is used to strengthen the growth of resistant strains). On stages E-35 and E-36, 1 LD (0.00018 gr) of thiodicarb are added, with a mortality rate of 25%. At the end of stage E-36 (growth strengthening stage for the resistant strains) the selection process reaches 1909 days of adaptation.

On stages E-37 and E-38, 0.9 LD (0.00000042 gr) of bifenthrin are added, with a mortality from 30 to 28% (The same way as in previous stages, E-38 is used to strengthen the growth of resistant strains). On stages E-39 and E-40, thiodicarb is increased to 1 LD (0.00000048 gr) decreasing mortality from 18 to 17%. At the end of stage 40 the selection process reaches 2015 days.

On stages E-41 and E-42, 1.1 LD (0.00020 gr) of thiodicarb are added, with a mortality from 18 to 17% (The same way as in previous stages, E-42 is used to strengthen the growth of resistant strains). On stages E-43 and E-44, 1.2 LD (0.00022 gr) of thiodicarb are added, with a mortality rate on both stages of 14%. At the end of stage E-44 (growth strengthening stage for the resistant strains) the selection process reaches 2016 days of adaptation.

On stages E-45 and E-46, 1.1 LD (0.00000054 gr) of bifenthrin are added, with a mortality from 15 to 12% (The same way as in previous stages, E-46 is used to strengthen the growth of resistant strains). On stages E-47 and E-48, thiodicarb is increased to 1.2 LD (0.00000060 gr) decreasing mortality from 10 to 7%. At the end of stage 48 (growth strengthening stage for the resistant strains) the selection process reaches 2182 days of adaptation.

TABLE NO. 3

Comparative Table, Initial and Final Characteristics
DEVELOPMENT CHARACTERISTICS *B. Thuringiensis*

| PARAMETER | INITIAL | FINAL |
| --- | --- | --- |
| pH | 4.5-5.5 | 7.2 |
| Humidity | 10% | 100% |
| Respiration | Anaerobic | Aerobic |
| Temperature | 30-37° C. | 25° C. |
| Resistant to: | Organochlorinated, organophosphorus compounds and mercury | 1.2 LD of thiodicarb and bifenthrin |
| Size | 1.0 × 3.0 μm | 1.0 × 3.0 μm |
| Biodegradation time | 120 days | 35 Days |

An important characteristic is that the aerotolerant condition of the *B. thuringiensis* is maintained under aerobiose conditions.

Carbohydrates from organic matter mineralize and stabilize in an average period of 35 days unlike the wild microorganism for which the time was 120 days.

Adaptation of the Carbohydrate Mineralization Microorganism Consortium in the Presence of Synthetic Carbamates and Pyretroids Work End Inoculum Production After finishing with the microorganism adaptation in presence of Thiodicarb and Bifenthrin, this mix is placed in a Malt Agar, Soy agar and SPC agar media for growing. Later, it is seeded and the growth and development is assessed for a quantitative determination. This value is used to determine the inoculum to be produced and applied to the organic fraction of household solid residues, livestock residues or agricultural residues.

As a result, and considering the final characteristics of the microorganism consortium resistant to thiodicarb (carbamate) and bifenthrin (pyrethroid), these microorganisms are added to the growth media in amounts that fall within the following ranges:

| | |
| --- | --- |
| *Bacillus brevis* | 10 to 25% |
| *Bacillus subtilis* | 20 to 25% |
| *Bacillus thuringiensis* | 25 to 40% |
| *Arthrobacter globiformis* | 25 to 30% |

After obtaining the previous mix with the lab microorganisms, it is transported in a conventional liquid growth media in appropriate containers that maintain their characteristics and properties. The microorganism concentration will be $2.5\text{-}3\times10^9$ CFU/ml.

INNOVATION SUMMARY

This innovation provides a consortium of resistant microorganisms to biodegrade carbohydrates present in the organic fraction of any solid residue source.

The genetic, metabolic and morphologic structure of these resistant microorganisms works efficiently biodegrading and mineralizing biodegradable solid residues from municipal or agricultural residues, reducing the gas and leachate production.

This compound enriches and increased the concentration of beneficial microorganisms, generating high quality biological fertilizers, suitable to be used in agricultural production, land restoration and conservation, under the parameters established by the sustainable organic agriculture where the conservation, restoration and use of nature or environment with no negative impact is desired.

The invention claimed is:

1. A consortium of microorganisms, wherein the microorganisms are initially exposed to a series of increasing fractions of a lethal dose of thiodicarb, subsequently exposed to a series of increasing fractions of a lethal dose of bifenthrin, wherein subsequent to the exposures of thiodicarb and bifenthrin, the microorganisms of the consortium are resistant to 1 to 1.3 times the lethal dose of thiodicarb and bifenthrin, wherein the consortium was deposited with the National Center of Genetic Resources (CM-CNRG) under accession number CM-CNRG TB44.

2. A consortium of microorganisms, wherein the microorganisms are initially exposed to increasing first fractions of a lethal dose of thiodicarb, subsequently exposed to increasing first fractions of a lethal dose of bifenthrin, subsequently exposed to increasing second fractions of a lethal dose of thiodicarb, wherein the second fractions of a lethal dose of thiodicarb are greater than the first fractions of a lethal dose of thiodicarb, subsequently exposed to increasing second fractions of a lethal dose of bifenthrin, wherein the second fractions of a lethal dose of bifenthrin are greater than the first fractions of a lethal dose of bifenthrin, subsequently exposed to increasing third fractions of a lethal dose of thiodicarb, wherein the third fractions of a lethal dose of thiodicarb are greater than the second fractions of a lethal dose of thiodicarb, subsequently exposed to increasing third fractions of a lethal dose of bifenthrin, wherein the third fractions of a lethal dose of bifenthrin are greater than the second fractions of a lethal dose of bifenthrin, subsequently exposed to increasing fourth fractions of a lethal dose of thiodicarb, wherein the fourth fractions of a lethal dose of thiodicarb are greater than the third fractions of a lethal dose of thiodicarb, subsequently exposed to increasing fourth fractions of a lethal dose of bifenthrin, wherein the fourth fractions of a lethal dose of bifenthrin are greater than the third fractions of a lethal dose of bifenthrin, subsequently exposed to increasing fifth fractions of a lethal dose of thiodicarb, wherein the fifth fractions of a lethal dose of thiodicarb are greater than the fourth fractions of a lethal dose of thiodicarb, and subsequently exposed to increasing fifth fractions of a lethal dose of bifenthrin, wherein the fifth fractions of a lethal dose of bifenthrin are greater than the fourth fractions of a lethal dose of bifenthrin, wherein subsequent to the first through fifth exposures of thiodicarb and the first through fifth exposures of bifenthrin, the microorganisms of the consortium are resistant to 1 to 1.3 times the lethal dose of thiodicarb and bifenthrin, wherein the consortium was deposited with the National Center of Genetic Resources (CM-CNRG) under accession number CM-CNRG TB44.

* * * * *